US010401263B2

(12) United States Patent
Clavaguera et al.

(10) Patent No.: US 10,401,263 B2
(45) Date of Patent: Sep. 3, 2019

(54) DEVICE FOR PICKING AND TRANSPORTING NANOOBJECTS CONTAINED IN AEROSOLS, WITH A CASSETTE WITH A MODULE SUITED TO REDUCING THE SUCTION NOISE DURING PICKING

(71) Applicant: COMMISSARIAT A L'ENERGIE ATOMIQUE ET AUX ENERGIES ALTERNATIVES, Paris (FR)

(72) Inventors: Simon Clavaguera, Grenoble (FR); Philippe Berne, Grenoble (FR); Arnaud Guiot, Saint Egreve (FR); Mathias Reynes, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 148 days.

(21) Appl. No.: 15/315,821

(22) PCT Filed: Jun. 3, 2015

(86) PCT No.: PCT/IB2015/054210

§ 371 (c)(1),
(2) Date: Dec. 2, 2016

(87) PCT Pub. No.: WO2015/186082

PCT Pub. Date: Dec. 10, 2015

(65) Prior Publication Data

US 2017/0102297 A1 Apr. 13, 2017

(30) Foreign Application Priority Data

Jun. 4, 2014 (FR) ..................................... 14 55053

(51) Int. Cl.
*G01N 1/22* (2006.01)

(52) U.S. Cl.
CPC ......... *G01N 1/2205* (2013.01); *G01N 1/2208* (2013.01); *G01N 2001/2223* (2013.01)

(58) Field of Classification Search
CPC ......... G01N 1/2205; G01N 2001/2223; G01N 1/2208; G01N 1/2273; G01N 15/0255;
(Continued)

(56) References Cited

U.S. PATENT DOCUMENTS 3,966,439 A * 6/1976 Vennos ................ G01N 1/2205
210/136
3,983,743 A * 10/1976 Olin ..................... G01N 1/2247
73/28.06

(Continued)

FOREIGN PATENT DOCUMENTS

WO WO2010033293 A1 3/2010
WO WO2012160263 A1 11/2012
WO WO2013050561 A1 4/2013

OTHER PUBLICATIONS

International Search Report in PCT/IB2015/054210 dated Aug. 18, 2015.

(Continued)

*Primary Examiner* — David A Rogers
(74) *Attorney, Agent, or Firm* — Jones Robb, PLLC

(57) ABSTRACT

A device for picking and transporting nano-objects present in an aerosol for analyzing includes a porous sampling filter configured to trap the nano-objects. The device also includes a cassette having means for holding the filter in a cavity within the cassette, an inlet orifice configured to allow aspirated aerosol to pass through, and an outlet orifice configured to pass the filtered aerosol, rid of the nano-objects trapped upstream of the inlet orifice of the cassette. A module of the device is configured to collect, by inertial impaction, the particles of a size above a threshold value and to allow aerosol containing particles of a size smaller than (Continued)

the threshold value to pass. The module is further configured to reduce, during picking, emission noise of the aspiration means of the picking device on which the cassette is fixed.

10 Claims, 4 Drawing Sheets

(58) Field of Classification Search
CPC ....... G01N 2001/2276; G01N 15/0272; G01N 1/2202; G01N 1/2247; G01N 2001/225; G01N 2001/2288
See application file for complete search history.

(56) References Cited

U.S. PATENT DOCUMENTS

| | | | | |
|---|---|---|---|---|
| 4,133,202 A * | 1/1979 | Marple | ............... | G01N 15/0255 73/28.04 |
| 4,155,247 A * | 5/1979 | Kaczmarek | .......... | G01N 1/2202 73/863.23 |
| 4,321,822 A * | 3/1982 | Marple | ................ | G01N 1/2208 73/28.06 |
| 4,350,037 A * | 9/1982 | Higham | ................ | G01N 1/2273 422/88 |
| 4,640,140 A * | 2/1987 | Burghoffer | ......... | G01N 15/0255 73/863.22 |
| 4,675,034 A * | 6/1987 | Lynch | ................ | G01N 1/2205 55/504 |
| 4,796,475 A * | 1/1989 | Marple | ................ | G01N 1/2205 422/70 |
| 4,827,779 A * | 5/1989 | Marple | ................ | G01N 1/2205 73/863.22 |
| 4,961,916 A * | 10/1990 | Lesage | ................... | B01D 53/30 422/109 |
| 5,333,511 A * | 8/1994 | Boyum | ................ | G01N 1/2273 323/299 |
| 5,977,547 A * | 11/1999 | Phillips | .................... | G01T 7/04 250/393 |
| 6,023,981 A * | 2/2000 | Phillips | ................ | G01N 1/2205 73/863.23 |
| 6,101,886 A * | 8/2000 | Brenizer | ................ | B01D 45/08 55/308 |
| 6,692,553 B2 * | 2/2004 | Jordan, Sr. | ............. | B01D 45/10 55/435 |
| 6,898,990 B2 * | 5/2005 | Rogers | ................ | G01N 1/2208 73/864.25 |
| 7,073,402 B2 * | 7/2006 | Trakumas | ............ | G01N 1/2208 73/863.22 |
| 7,334,453 B2 | 2/2008 | Trakumas et al. | | |
| 7,597,015 B2 * | 10/2009 | Harley | ................ | G01N 1/2208 73/28.05 |
| 8,584,536 B2 * | 11/2013 | Page | .................... | G01N 1/2205 73/863.24 |
| 8,584,795 B1 | 11/2013 | Buckner | | |
| 8,689,648 B1 | 4/2014 | Heff | | |
| 8,991,271 B2 * | 3/2015 | Uang | ................... | G01N 1/2202 73/863.22 |
| 9,086,341 B2 * | 7/2015 | Tsai | ..................... | G01N 1/2208 |
| 9,109,980 B2 * | 8/2015 | Ewing | ................ | G01N 1/2214 |
| 9,457,348 B2 * | 10/2016 | Clavaguera | .......... | G01N 1/2205 |
| 9,506,843 B2 * | 11/2016 | Peters | .................. | G01N 1/2208 |
| 9,534,989 B2 * | 1/2017 | Page | .................... | G01N 1/2205 |
| 2004/0216612 A1 | 11/2004 | Dennis | | |
| 2007/0044577 A1 | 3/2007 | Trakumas et al. | | |
| 2009/0272202 A1 | 11/2009 | Uang et al. | | |

OTHER PUBLICATIONS

Marple, V.A, et al. "Impactor Design", Atmospheric Environment, 1976, vol. 10, pp. 891-896.

* cited by examiner

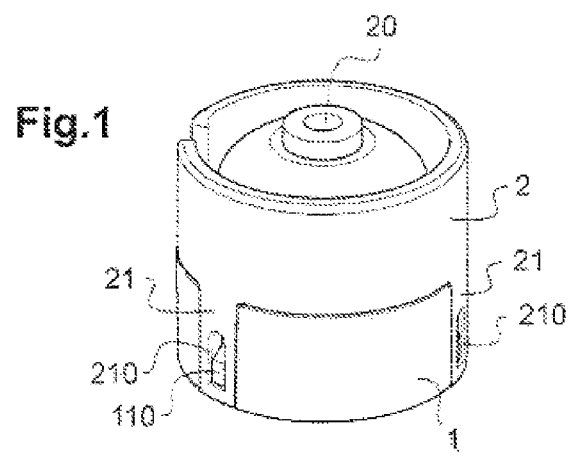
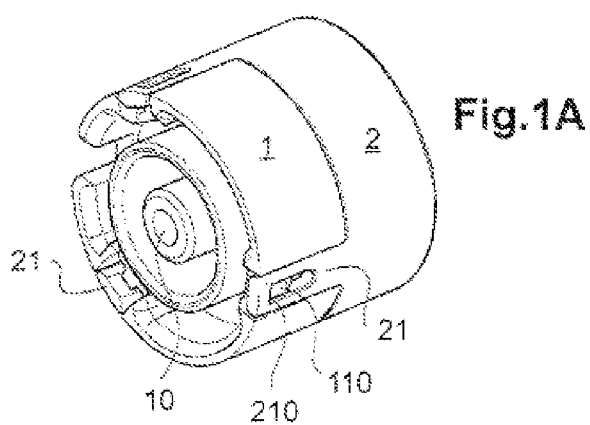
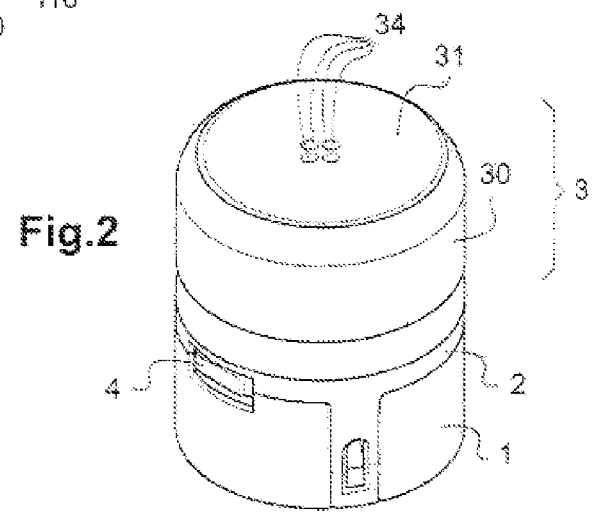

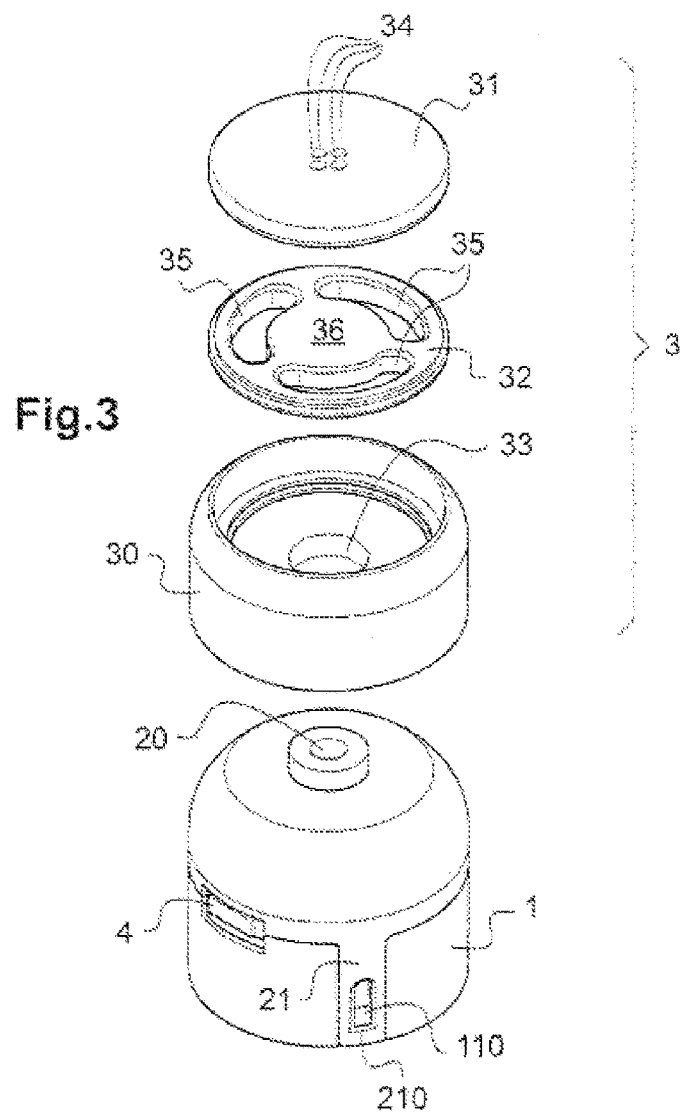
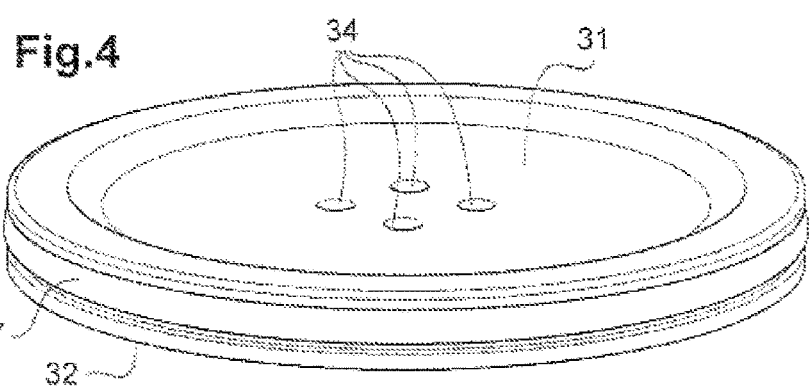

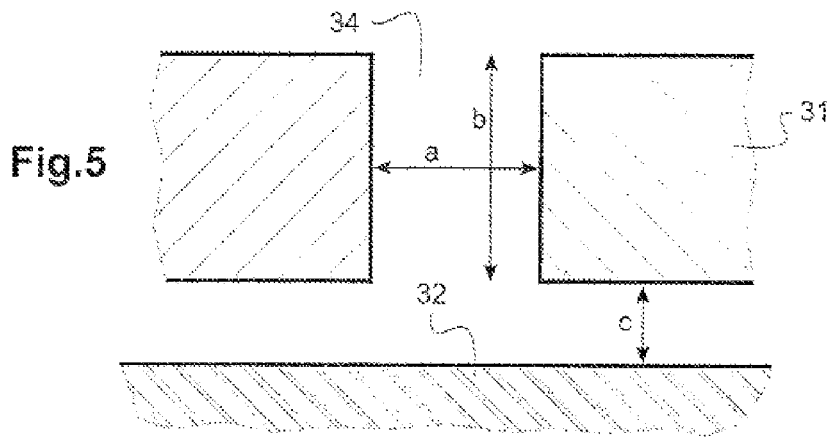
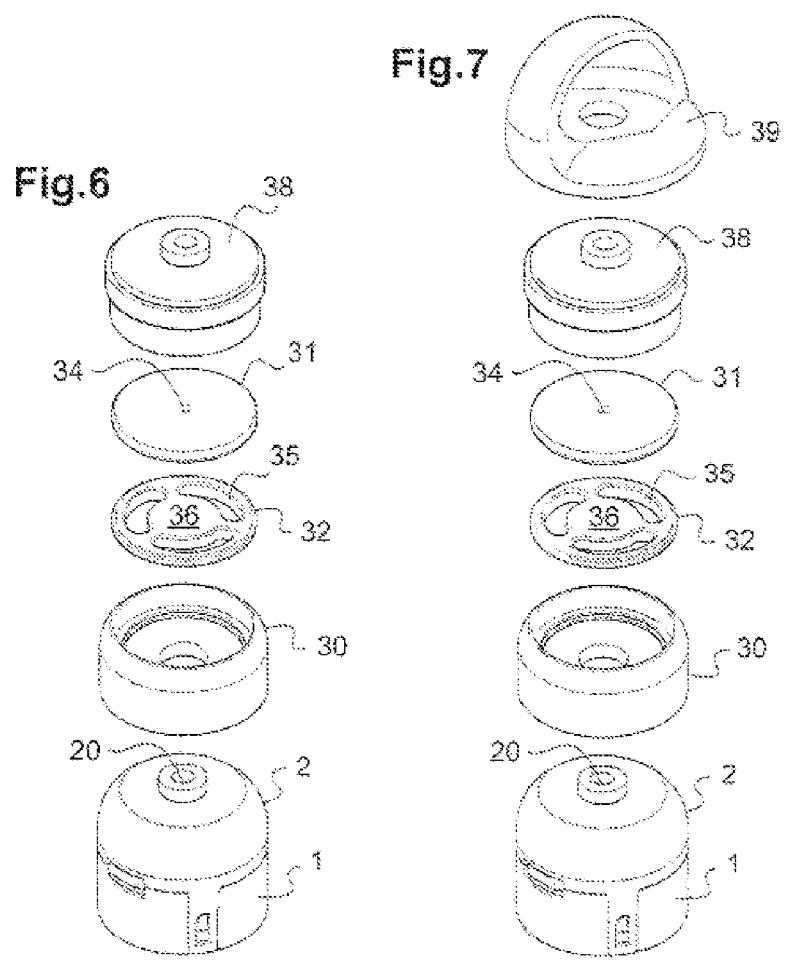

DEVICE FOR PICKING AND TRANSPORTING NANOOBJECTS CONTAINED IN AEROSOLS, WITH A CASSETTE WITH A MODULE SUITED TO REDUCING THE SUCTION NOISE DURING PICKING

This application is a national stage application of International PCT Application No. PCT/IB2015/054210, filed internationally on Jun. 3, 2015, which claims priority to French Application No. FR 14 55053, filed Jun. 4, 2014, the entire content of each of which is incorporated by reference herein in its entirety.

TECHNICAL FIELD

The present invention concerns the field of collection and analysis of nanoparticles liable to be present in suspension in the air.

More particularly, it concerns the design of a device for sampling and transporting of nano-objects contained in aerosols, with a sampling cassette.

The present invention aims to reduce the noise emitted during the sampling, and aspiration means which are integrated in the sampling apparatus in which the sampling cassette is secured in a removable manner.

PRIOR ART

The rapid rise of nanotechnologies is making it necessary to look into the health and environmental impacts of these new materials in order to have optimal safety conditions. For several years, nanoparticles, or particles with nanometer dimensions, have been the subject of intense research and their use has begun to spread into various fields such as health, microelectronics, energy technologies or ordinary consumer products such as paints and cosmetics. It is therefore necessary to create methods for evaluation and monitoring of the exposure of workers, consumers and the environment to nanoparticles.

The development of reliable methods of sampling and analysis of nanometer aerosols is thus a crucial issue in terms of public health and prevention of risks on the job site. In particular, the development of sampling devices adapted to be portable and secured as a unit to the work clothes of a worker at a station for the manufacture of nano-objects or the processing of nano-materials, or of products containing them, might prove to be mandatory.

The method of choice for sampling, or the one which is preferable at present, consists in aspirating a flow of air liable to be laden with particles through a filter which is then analyzed by various techniques (gravimetry, microscopy, XRF, etc.).

In the prior art, sampling devices also known as cassette samplers are already known, being portable and meant to sample an aerosol contamination liable to be inhaled through the mouth and the nose of an individual during his respiration.

A sampler is a device which comprises in particular means of aspiration and on which is secured, generally in removable manner, a sampling cassette holding at least one filter for sampling of contaminants by aspiration.

Sampling by collection of particles with a combined method of aspiration and inertial impact is known. Inertial impact is the mechanism by which particles which have a tendency to circulate in the initial direction of their movement will deviate from their lines of flow to impact against a surface.

For example, one may refer to the publication [1] which illustrates the fact that the scientific and technical community have been developing inertial impact devices for around thirty years. In particular, FIG. 1 of this publication diagrams the lines of flow and the trajectory taken by particles in the case of a hole-type impactor, with determining dimensions to define the cutoff threshold of this type of impactor. Thus, the size selection of particles by inertial impact is known, more particularly, for micron and nanometer particles.

The patent U.S. Pat. No. 7,334,453 concerns a sampling device for particles by inertial impact. The company which holds this patent has furthermore published a certain number of documents regarding this device. It thus emerges that this device is comprised of a single impact plate and is able to select particles in suspension in the surrounding air, the particles being of size referenced as $PM_{10}$ (particles down to 10 μm in diameter), $PM_{2.5}$ (particles down to 2.5 μm in diameter) and $PM_{course}$ (particles of diameter between 2.5 and 10 μm). The device disclosed can be used for a flow rate of 10 L/min. In such a device, the largest particles are collected on the impact plate, previously greased, while the finest particles are collected on a filter of 47 mm diameter. The filter as well as the impact plate are lodged in a housing which can be used directly in-situ and which is disposable.

Furthermore, it is recommended by the public health authorities to conduct the sampling of nano-objects in a zone defined as being the "respiratory sphere" of the person who is wearing a sampler. Thus, this respiratory sphere is a zone of 30 cm radius around entrances of the respiratory passages (nose, mouth). This implies then that the sampler may comprise an individual sampling pump which is portable so that it can be placed relatively close to the face, that is, in the respiratory sphere.

Now, the inventors have found that the wearing of such a pump is a nuisance in terms of work ergonomics. In particular, the movements of the person may be hampered, the weight of several hundred grams of a pump cannot be worn for long, and in particular the pump emits continuous emission noise during its sampling operation, which may be annoying.

In many applications where air is aspirated, it is known how to make filters with a noise reducer (acoustic silencing).

Thus, the patent U.S. Pat. No. 8,584,795B1 concerns a silent filter for humid air compressors or air blowers. The silent filter disclosed is comprised of two distinct parts mounted in a common envelope delimiting a chamber. In regard to the direction of flow, the most upstream part serves as a filter, while the most downstream part plays the role of an acoustic silencer. The acoustic silencer is comprised of a stack of plates having openings forcing the flow to pass through baffles. Thus, the flow of air comes in through the entrance of the silencer chamber and then the flow is divided by a deflector into several small flow jets by semi-circular openings inside a first baffle. This silencer structure thus assists in reducing the noise of the assembly.

Patent application WO 2012/160263A1 concerns an apparatus for filtering and sterilizing of ambient air whose operating principle is based on mechanical purification: the particles present in the air impact against the numerous fibers of the filters which are present. In order to have good efficiency, the apparatus is outfitted with a powerful fan which produces a level of sonic emission liable to be inconvenient if not treated. Thus, the apparatus disclosed comprises an acoustic silencer adapted to reduce the sound level of the aeraulic system.

It emerges from a study of the prior art that no device has been proposed which is able to significantly reduce the emission of suction sound of an individual sampling pump of a sampler with a removable sampling cassette housing at least one sampling filter for nano-object contaminants by aspiration.

The general purpose of the invention is thus to mitigate some or all of the drawbacks of the prior art and especially to reduce the emission noise of the means of aspiration of a sampling apparatus to which there is secured a cassette of a device for sampling and transporting of nano-objects liable to be present in an aerosol.

One particular purpose of the invention is to propose a device which answers the general purpose and moreover is simple to produce and low in cost.

Explanation of the Invention

To accomplish this, the invention first of all involves a device for sampling and transporting of nano-objects liable to be present in an aerosol for purposes of their analysis, comprising:
 a porous sampling filter able to trap nano-objects liable to be in suspension in the aerosol,
 a cassette comprising means of holding the filter in a cavity inside it, an entrance orifice able to let pass the aerosol by aspiration through the filter, and an exit orifice able to let the aspirated air emerge without the trapped nano-objects.

According to the invention, the device comprises, upstream from the entrance orifice of the cassette, an inertial impact module distinct from the cassette and able on the one hand to collect by inertial impact particles with a size above a threshold value and to let pass the aerosol containing particles with a size smaller than the threshold value, and on the other hand to reduce during the sampling process the noise emitted by the means of aspiration of the sampling apparatus to which the cassette is secured.

In other words, the module according to the invention enables a selection of particles by size thanks to inertial impact, but it also is able to significantly reduce the noise emitted by the pump.

The particles selected thus enable a monitoring of the quality of the ambient air of an environment, especially a work environment in which (nano)particles are being handled.

According to one advantageous embodiment, the module is a tight assembly of the following elements:
 a body with a central orifice in communication with the entrance orifice of the cassette,
 a first plate, or inertial impact plate, held inside the body, and comprising a central solid portion and elongated openings at its periphery in communication with the central orifice of the body,
 a second plate, or selector plate, held inside the body above the inertial impact plate, and comprising one or more holes distributed in a circle around its center, the holes being in communication with the elongated openings.

The diameter (a) of the holes is preferably between 0.1 and 1.5 mm.

The thickness (b) of the selector plate defining the length of the holes is for its part preferably between 0.5 and 2 mm, and the spacing (c) between the selector plate and impact plate is between 0.1 and 1 mm.

According to one advantageous variant, the module comprises a sampling head on top of the module in communication with the outside.

Advantageously, the sampling head comprises a deflector able to modify the angle of sampling with respect to the longitudinal axis of the cassette.

The module may be secured in a removable manner or in a permanent manner to the cassette.

The invention likewise concerns the use of a device just described as an assembly for tracking the exposure of workers at a manufacturing station for nano-objects, processing of nano-materials, or of products containing them.

DETAILED DESCRIPTION

Other advantages and characteristics will become more clear from a perusal of the detailed description, given as an illustration and not a limitation, making reference to the following figures in which:

FIG. 1 is a profile view of the sampling cassette of a portion of a sampling device according to the invention, the cassette being in the assembled configuration, FIG. 1A is a bottom view of the cassette according to FIG. 1;

FIG. 2 is a perspective view of the sampling device according to the invention with the sampling cassette according to FIGS. 1 and 1A to which is secured an inertial impact and noise reduction module according to the invention;

FIG. 3 is a partially exploded view of the device according to FIG. 2 showing the constitution of the inertial impact and noise reduction module according to the invention;

FIG. 4 is a perspective view showing a selector plate which, associated with an impact plate, constitutes an inertial impact and noise reduction module according to the invention;

FIG. 5 is a schematic view in partial section of an inertial impact and noise reduction module according to the invention;

FIG. 6 is an exploded perspective view showing an inertial impact and noise reduction module according to the invention provided with a sampling head according to a first variant, on top of a sampling cassette;

FIG. 7 is an exploded perspective view of a sampling head according to a second variant, with deflector, on top of a sampling cassette;

FIG. 8 is an exploded perspective view showing an inertial impact and noise reduction module according to the invention, utilized without sampling cassette;

FIG. 9 is a graph characterizing the effectiveness of deposition of nanoparticles as a function of their aerodynamic diameter of an inertial impact and noise reduction module according to the invention;

Throughout the present application the terms "vertical", "lower", "upper", "bottom", "top", "below", "above", "height" are to be understood in regard to a sampling device with the cassette disposed along the vertical with the entrance orifice on top.

Likewise, the terms "entrance", "exit", "upstream" and "downstream" are to be understood in regard to the direction of aspiration flow through the sampling device.

In order to carry out a sampling of nano-objects liable to be contained in an aerosol, the device according to the invention comprises first of all a filter, not shown, which is adapted to trap nano-objects liable to be in suspension in the air, being lodged and held in a cavity formed by a cassette in the closed configuration.

Thus, the sampling method according to the invention consists in orienting the closed cassette so that the air being analyzed is aspirated by a pump, not shown, which is integrated in a sampling apparatus to which the cassette is attached, the air being aspirated from an orifice 20 and emerging from the cassette through the orifice 10 and then going to the pump.

The aspiration can of course be provided along the reverse path, that is, from the orifice 10 to the orifice 20. The nano-objects or particles of micrometer size so aspirated will be collected on the filter held in the cassette. In the method of sampling according to the invention, one may arrange for the cassette to be oriented so that the sampling is as representative as possible of the respiration through the mouth or through the nose. Thus, preferably, to simulate a respiration through the nose, the cassette is oriented so that it is vertical with the aspiration orifice 20 at the bottom and thus there is an aspiration from bottom to top. Likewise, preferably to simulate a respiration through the mouth, the cassette is oriented to have the aspiration orifice 20 horizontal.

As is represented, the device according to the invention allows a collecting of a sample and the transporting of the trapped nano-objects in a secured manner with perfect traceability.

An assembly for sampling and transporting nano-objects thus comprises the device with cassette and filter according to the invention and a sampling apparatus to which the cassette is secured during the sampling and which integrates the aspiration pump.

As is illustrated in FIGS. 1 to 2, the cassette is composed of two pieces 1, 2 of general cylindrical shape.

The upper piece 2 is provided with feet 21 which are flexible, in other words elastically deformable, whose end comprises an opening 210.

The lower piece 1 is provided with cavities 11 which are individually complementary to a foot 21 with one end comprising a protrusion individually complementary to an opening 210. Of course, in the scope of the invention one can provide an arrangement of complementary openings or protrusions in the reverse manner, that is, with protrusions individually in a cavity of the piece 2 and feet with openings on the piece 1.

The angular arrangement between the flexible feet 21 of the upper piece 2 is identical to that of the cavities 11 of the lower piece 1.

Thus, in the mutual assembled configuration, the feet 21 with their openings 210 fit into and are clipped precisely in the cavities 11 and around the protrusions 110 (FIGS. 1 and 1A).

One may refer to the patent application filed this day by the applicant and entitled "Assembly for sampling and transporting nano-objects contained in aerosols, with a cassette the opening of which is secured during the sampling", involving an advantageous embodiment for the fixation of such a cassette to a sampling apparatus.

As for the filter, this is supported by a filter holder 4. In the assembled configuration of the two pieces 1, 2, the filter holder is held squeezed between two shoulders each produced on an internal periphery of one of the two pieces 1, 2.

Advantageously, the filter holder 4 is chosen from an elastically deformable material and it then plays the supplemental role of a gasket between the lower 1 and upper 2 pieces of the cassette. In other words, one can advantageously provide a filter holder of less hardness than the materials of the pieces 1 and 2 of the cassette, in order to be flattened against the opposite shoulders by pressure during the clipping process. As the filter holder 4 has the role of being a mechanical support for the filter, it can have an overall annular conformation or be made from a single massive piece traversed by a plurality of holes emptying into straight channels in the thickness of the piece, this plurality of holes then forming the filter proper.

In any case, one will make sure to generate the minimum of head losses in the area of the aspiration.

The inventors have discovered that during a sampling with the cassette represented in FIGS. 1 and 1A the aspiration pump would emit a continuous emission noise, the level of which was not acceptable to a user.

Furthermore, they were interested in the collecting of nanoparticles by inertial impact.

Surprisingly, by testing out a module adapted to inertial impact attached to the cassette, upstream from the entrance orifice 20, they were able to determine a notable reduction in the noise emitted by the aspiration pump.

Thus, according to the invention, as illustrated in FIGS. 2 and 3, there is provided a module 3 able, on the one hand, to collect by inertial impact particles of a size above a threshold value and to let pass the aerosol containing particles with size below the threshold value, and on the other hand to reduce, during the sampling process, the noise emitted by the aspiration means of the sampling apparatus to which the cassette 1, 2 is secured.

In other words, the module 3 according to the invention, attached to the cassette 1, 2 upstream from the entrance orifice 20, is able both to reduce the noise in the operating phase during the sampling and to select the size of the particles so sampled and being representative of an aerosol liable to be inhaled by a person.

FIGS. 2 and 3 show a sample embodiment of an inertial impact and noise reduction module 3 according to the invention. Such a module 3 is formed by a stack of various pieces.

A tight body 30 receives and mechanically positions an impact plate 32 on top of which is disposed a selector plate for particles 31.

The tight body 30 has a central orifice 33 in communication with the entrance orifice 20 of the upper piece 2 of the cassette, when the module 3 is on top of the cassette 1, 2.

The selector plate 31 has one or more calibrated holes 34 around its central portion.

The impact plate 32 comprises a solid central portion 36 and oblong openings 35 at its periphery.

When the module 3 is assembled, the central portion 36 is arranged opposite the calibrated holes 34 and the openings 35 are in communication with the central orifice 33 of the body 30.

As shown in FIG. 4, an O-ring 37 is advantageously provided between the plate 32 and the tight body 30.

A step, not shown, which is made at the periphery, is required in order to separate the plates 31 and 32 by a precise distance in order to guarantee the distance between the calibrated holes 34 and the opposite impact plate 32.

The inventors were able to determine that the diameter (a) of the calibrated holes 34 of the selector plate 31, their number, the thickness of the plate (b) as well as the distance (c) between the plates 31 and 32 are parameters to be controlled, and which can be modified in order to achieve a good compromise between collection of particles and noise reduction, as stipulated in the following examples. The parameters (a), (b) and (c) are represented schematically in FIG. 5.

Preferably, one selects the following ranges for the parameters:
(a): between 0.1 and 1.5 mm;
(b): between 0.5 and 2 mm
(c): between 0.1 and 1 mm.

According to one variant embodiment, as illustrated in FIG. 6, the module 3 may comprise a sampling head 38 which will be positioned on top of the selector plate 31.

The sampling head 38 may comprise a deflector 39 which allows a modifying of the angle of the axis of sampling. The modification of the sampling angle can be at any given angle, such as 90° as shown in FIG. 7.

Depending on the materials making up the different pieces of the module 3, such as metal, polymer, or other, advantageously dissipating electrical charges, the supporting of these various pieces 30, 31, 32, 38 as well as the tightness between them can be ensured by different means. One can contemplate connections by tight fitting, soldering, gluing, sealing, and so on. One will make sure that the means of support are compatible with the method of fabrication, such as machining, molding, 3D printing, etc.

The assembled module 3 can be secured removably or otherwise to a sampling cassette 1, 2 while also ensuring the mechanical support and the tightness of the overall device. One can contemplate a mounting of the module 3 on the cassette 1, 2 by tight fit, screw fastening, welding or gluing, etc.

The inventors tested out various geometrical configurations of the pieces 30, 31, 32 of the module 3 according to the invention.

More precisely, the geometry and the number of holes 34 of the selector plate 31 in order to evaluate the changes in the resulting sound attenuation.

The tests were carried out with:
a commercial pump operating at a flow rate of 0.6 L/min;
a cassette housing a filter made of polycarbonate.

The sound attenuation was measured in dBA at a distance of 30 cm from the cassette device 1, 2 topped with the module 3, with the pump in operation and connected by a hose to the device via the exit orifice 10 of the cassette and exported for the measurement at a distance of 2 m from the cassette.

The test results are given in the following table.
In this table:
X is the reference of the particular selector plate 31.
n is the number of holes 34 distributed at the center of the plate for n=1 and uniformly on a circle for n>1, that is, arranged at angles of $\pi/n$ in relation to the center of the plate 31, or 180° for two holes 34, 120° for three holes 34; 90° for four holes 34. The radius of the circle on which they are distributed is between 1 and 4 mm, preferably equal to 3.7 mm,
d is the diameter of the holes in mm.

TABLE

| X | n holes 34 disposed at $\pi/n$ degrees around the center of the plate 31 | d (mm) | sound level (dBA) |
|---|---|---|---|
| A | 1 | 0.64 | 51.65 |
| B | 1 | 1.83 | 60.0 |
| C | 2 | 1.04 | 57.7 |
| D | 2 | 1.61 | 61.4 |
| E | 3 | 0.51 | 53.4 |
| F | 3 | 1.27 | 61.7 |
| G | 4 | 0.53 | 55.5 |
| H | 4 | 1.12 | 58.4 |
| I | 4 | 1.43 | 62.5 |
| J | 6 | 0.52 | 56.8 |

For comparison, the sound level measured at the exit of the sampling cassette 1.2 without module 3 is 75 dBA.

It emerges from the table above that the sound attenuation provided by the module 3 according to the invention varies from 51 to 62 dBA for a number of holes between 1 and 6.

The inventors then tested a selector plate 31 according to reference H in terms of selection of particles.

The choice was made for this plate 31 per reference H because it has four holes which allow an improved representative nature of the sampling and a medium attenuation. Furthermore, a plate 31 with four holes 34 makes it possible to limit the risks of fouling and re-entrainment of the particles collected.

Figures 8, 9:
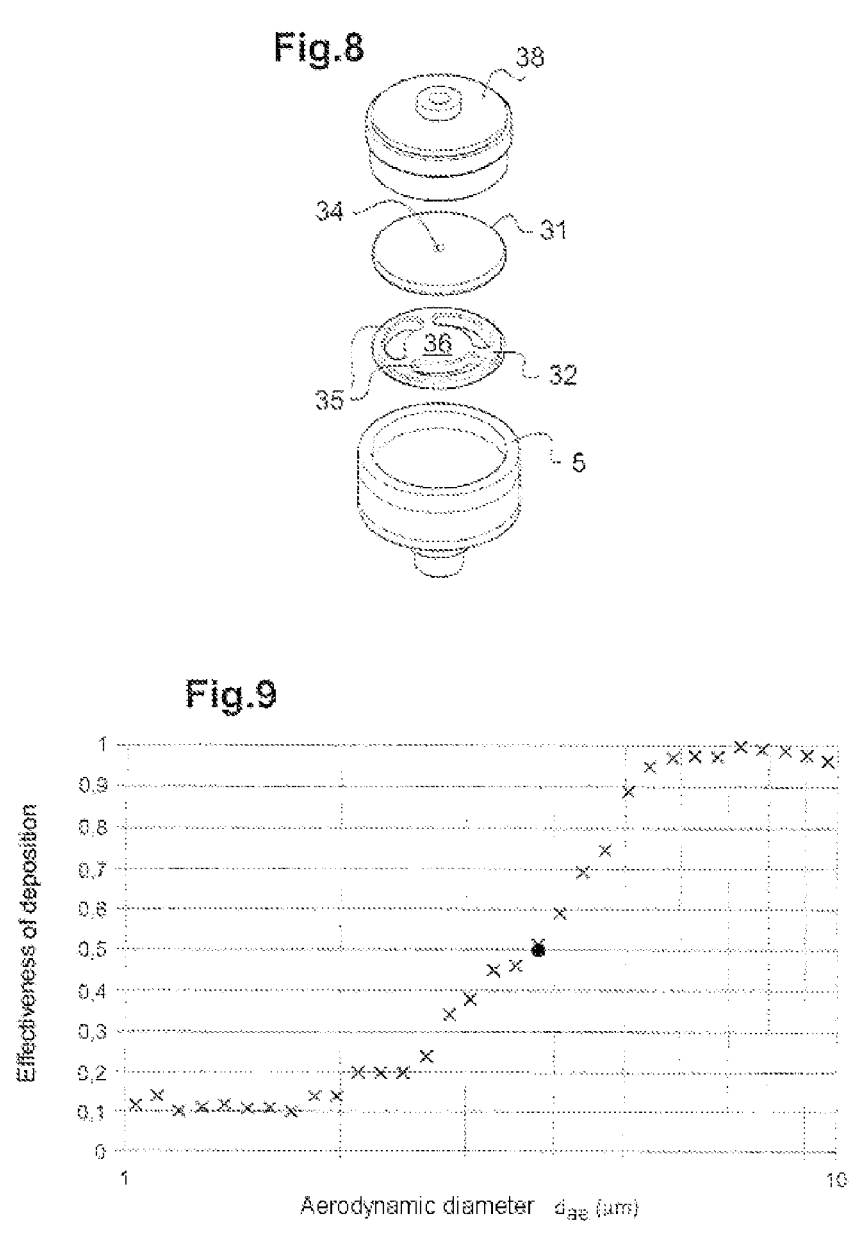

The plate 31 per reference H of the above table makes it possible to obtain a size selection of the particles according to the graph shown in FIG. 9.

The abscissa shown in FIG. 9 indicates the aerodynamic diameter of a particle in a fluid, defined as the diameter equivalent to a sphere of density equal to 1 g/cm$^3$ and having the same aerodynamic behavior.

Upon perusal of this graph, the experimental results of the tested plate 31 per reference H indicate a cut-off diameter, that is, a diameter beyond which at least 50% of the particles are impacted by the plate 32, of 3.6 µm.

The critical dimensions of the selector plate 31 and impact plate 32 and between the two are as follows:
a=1.12 mm
b=1 mm
c=0.5 mm
n=4.

The module 3 just described according to the invention enables both
significant reduction in the sound emission during the aspiration yet without generating additional head losses in the sampling device and without making it heavier;
size selection of the particles, the principle of inertial impact with different geometries (number of holes, distance between the holes 34 of the selection plate 31 and impact plate 32) enabling an adjusting of the cut-off diameter ($D_{50\%}$).

Other variants and improvements can be made without thereby leaving the scope of the invention.

More particularly, although the module 3 according to the invention has been used in the context of the invention with a sampling cassette of two pieces 1, 2, one can implement such a module by itself, with only a selector plate 31 and an impact plate 32 with a controlled spacing c between them and a controlled tightness so as to select particles according to size, yet without collecting particles which pass to a downstream filter.

In other words, the module 3 can be used by itself, without cassette 1, 2, or connected to any given geometry of cassette by any given means (hose, etc.), or connected to a real-time counter. FIG. 8 represents a variant of an inertial impact and noise reduction module 3 according to the invention, utilized without a sampling cassette. In this illustrated variant, a sampling head 38 is provided, which will be positioned on top of the selector plate 31 and the two plates 31, 32 are housed and supported in tight manner inside an aspiration hose nozzle 5 provided for this purpose.

The invention is not limited to the examples just described; in particular, one can combine the characteristics of the examples illustrated in the context of variants which have not been illustrated.

REFERENCE CITED

[1]: Marple & Willeke "*Impactor Design*" Atmospheric Environment (1976) Vol. 10, pp 891-896.

The invention claimed is:

1. A device for sampling and transporting nano-objects present in an aerosol for purposes of analysis, comprising:

a porous sampling filter configured to trap nano-objects in suspension in the aerosol, a cassette comprising means for holding the filter in a cavity formed by the cassette, an entrance orifice configured to pass aspirated aerosol through the filter, and an exit orifice configured to let the aspirated aerosol emerge without trapped nano-objects, the cassette configured to be secured to a sampling apparatus comprising an aspiration means, upstream from the entrance orifice of the cassette, a module distinct from the cassette and configured to collect, by inertial impact, particles with a size above a threshold value and to let pass the aerosol containing particles with a size smaller than the threshold value, and further configured to reduce, during the sampling process, noise emitted by the aspiration means of the sampling apparatus.

2. A device for sampling as claimed in claim 1, wherein the module is an assembly of the following elements:

a body with a central orifice in communication with the entrance orifice of the cassette, a first plate, or inertial impact plate, held inside the body, and comprising a central solid portion and elongated openings at a periphery of the inertial impact plate, the openings being in communication with the central orifice of the body, a second plate, or selector plate, held inside the body above the inertial impact plate, and comprising one or more holes distributed in a circle around a center of the selector plate, the holes being in communication with the elongated openings.

3. A device for sampling as claimed in claim 2, wherein a diameter of the holes is between 0.1 mm and 1.5 mm.

4. A device for sampling as claimed in claim 2, wherein a thickness of the selector plate defining a length of the holes is between 0.5 mm and 2 mm.

5. A device for sampling as claimed in claim 2, wherein a spacing between the selector plate and impact plate is between 0.1 mm and 1 mm.

6. A device for sampling as claimed in claim 2, wherein the module comprises a sampling head on top of the module in communication with an environment outside the module.

7. A device for sampling as claimed in claim 6, wherein the sampling head comprises a deflector configured to modify an angle of sampling with respect to a longitudinal axis of the cassette.

8. A device for sampling as claimed in claim 1, wherein the module is secured in a removable manner to the cassette.

9. A device for sampling as claimed in claim 1, wherein the module is secured in a permanent manner to the cassette.

10. Use of a device as claimed in claim 1 as an assembly for tracking exposure of workers at a manufacturing station for nano-objects, processing of nano-materials, or of products containing nano-objects or nano-materials.

* * * * *